US010987366B2

(12) United States Patent
Grdina

(10) Patent No.: US 10,987,366 B2
(45) Date of Patent: *Apr. 27, 2021

(54) METHODS AND COMPOSITIONS FOR PROTECTION OF CELLS AND TISSUES FROM COMPUTED TOMOGRAPHY RADIATION

(71) Applicant: The University of Chicago, Chicago, IL (US)

(72) Inventor: David J. Grdina, Naperville, IL (US)

(73) Assignee: The University of Chicago, Chicago, IL (US)

( * ) Notice: Subject to any disclaimer, the term of this patent is extended or adjusted under 35 U.S.C. 154(b) by 7 days.

This patent is subject to a terminal disclaimer.

(21) Appl. No.: 15/862,171

(22) Filed: Jan. 4, 2018

(65) Prior Publication Data

US 2018/0193363 A1    Jul. 12, 2018

Related U.S. Application Data

(63) Continuation of application No. 13/822,223, filed as application No. PCT/US2011/051946 on Sep. 16, 2011, now Pat. No. 9,877,976.

(60) Provisional application No. 61/383,592, filed on Sep. 16, 2010.

(51) Int. Cl.
| | | |
|---|---|---|
| A61K 49/00 | (2006.01) | |
| A61K 31/661 | (2006.01) | |
| A61K 31/132 | (2006.01) | |
| A61K 31/355 | (2006.01) | |
| A61K 33/04 | (2006.01) | |
| A61K 45/06 | (2006.01) | |
| A61B 6/00 | (2006.01) | |
| A61B 6/03 | (2006.01) | |
| A61K 31/145 | (2006.01) | |

(52) U.S. Cl.
CPC ............ *A61K 31/661* (2013.01); *A61B 6/032* (2013.01); *A61B 6/508* (2013.01); *A61K 31/132* (2013.01); *A61K 31/145* (2013.01); *A61K 31/355* (2013.01); *A61K 33/04* (2013.01); *A61K 45/06* (2013.01); *A61K 49/0008* (2013.01)

(58) Field of Classification Search
CPC .... A61K 31/00; A61K 31/661; A61K 31/145; A61K 31/132; A61K 31/355; A61K 6/00; A61K 6/032; A61K 6/508; A61K 49/00; A61K 49/0008; A61K 33/00; A61K 33/04; A61K 45/00; A61K 45/06; A61K 2300/00
USPC ................. 424/1.11, 1.65, 1.69, 9.1, 9.2, 9.3
See application file for complete search history.

(56) References Cited

U.S. PATENT DOCUMENTS

| | | | | |
|---|---|---|---|---|
| 5,488,042 A | * | 1/1996 | Grdina | ................... A61K 31/13 514/114 |
| 5,567,686 A | | 10/1996 | Grdina | ........................... 514/43 |
| 5,869,338 A | | 2/1999 | Grdina | .......................... 435/375 |
| 5,891,856 A | | 4/1999 | Grdina | ........................... 514/43 |
| 6,984,619 B1 | | 1/2006 | Grdina et al. | ..................... 514/1 |
| 9,877,976 B2 | * | 1/2018 | Grdina | ................. A61K 31/132 |
| 2003/0114379 A1 | * | 6/2003 | Li | ...................... A61K 41/0038 530/351 |

FOREIGN PATENT DOCUMENTS

WO    WO/1995/007700    3/1995

OTHER PUBLICATIONS

Koukourakis et al, Anticancer Research, vol. 26, pp. 2437-2444. (Year: 2006).*
Saynak et al, Cancer Therapy, vol. 4, pp. 283-288 (Year: 2006).*
Benz et al., "Reduction of cancer risk associated with pediatric computed tomography by the development of new technologies", *Pediatrics*, 114(1):205-209, 2004.
Bhatti et al., *Radiat. Environ. Biophys.*, 49(4) :685-692, 2010.
Brenner et al., *Am. J. Roentgenol.*, 176(2):289-296, 2001.
Brody et al., *Pediatrics*, 120(3): 677-682, 2007.
Durante et al., *Nature Reviews*, 8:465-472, 2008.
Dziegielewski et al, "Amifostine metabolite WR-1065 disrupts homologous recombination in mammalian cells", *Radiation Research*, 173(2):157-183, 2010.
Dziegielewski et al., "WR-1065, the active metabolite of amifostine, mitigates radiation-induced delayed genomic instability", *Free Radical Biology & Medicine*, 45(12):1674-1681, 2008.
Hooker et al., "Low doses of amifostine protect from chromosomal inversions in spleen in vivo when administered after an occupationally relevant X-radiation dose", *International Journal of Low Radiation*, 6(1):43-56, 2009.
Hosseinimehr, "Potential utility of radioprotective agents in the practice of nuclear medicine", *Cancer Biotherapy & Radiopharmaceuticals*, 24(6):723-731, 2009.
Huang et al., "Whole-body PET/CT scanning: estimation of radiation dose and cancer risk", *Radiaology*, 251(1):166-174, 2009.
Huang et al., *Molec. Cell. Biol.*, 24(11) :5060-5068, 2004.
International Preliminary Report on Patentability issued in PCT Application No. PCT/US2011/051946, dated Mar. 19, 2013.
International Search Report and Written Opinion issued in PCT Application No. PCT/US2011/051946, dated Mar. 28, 2012.

(Continued)

*Primary Examiner* — D. L. Jones
(74) *Attorney, Agent, or Firm* — Norton Rose Fulbright US LLP

(57) ABSTRACT

Described are methods for preventing or inhibiting genomic instability and in cells affected by diagnostic radiology procedures employing ionizing radiation. Embodiments include methods of preventing or inhibiting genomic instability and in cells affected by computed tomography (CT) radiation. Subjects receiving ionizing radiation may be those persons suspected of having cancer, or cancer patients having received or currently receiving cancer therapy, and or those patients having received previous ionizing radiation, including those who are approaching or have exceeded the recommended total radiation dose for a person.

19 Claims, 12 Drawing Sheets

Specification includes a Sequence Listing.

(56) References Cited

OTHER PUBLICATIONS

Jonese et al., *Radiat. Res.*, 158(4) :424-442, 2002.
Kataoka et al., *Radiat. Res.*, 168 :106-11, 2007.
Khamsi, *New Scientist*, May 11, 2007.
Kim et al., *Cancer Res.*, 66 :10377-10383, 2006.
Kumar et al., *Radiat. Res.*, 165(1) :43-50, 2006.
Lamperti et al., *Radiat. Res.*, 124 :194-200, 1990.
Li et al., *Prostate*, 35 :221-233, 1998.
Limoli et al., *Cancer Res.* 57(18) :4048-4056, 1997.
Marder and Morgan, *Mol. Cell. Biol.*, 13(11):6667-6677, 1993.
Miller et al., "Conputed tomographic assessment of radiation induced damage in the lung of normal and WR 2721 protected LAF1 mice", *International Journal of Radiation: Oncology Biology Physics*, 12(11):19711975, 1986.
Morgan, *Radiat. Res.*, 159(5):567-580, 2003a.
Murley et al., *Radiat. Res.*, 158(1) :101-109, 2002.
Murley et al., *Radiat. Res.*, 162 :536-546, 2004.
Murley et al., *Radiat. Res.*, 167 :465-474, 2007.
Murley et al., *Radiat. Res.*, 169 :495-505, 2008.
Murley et al., *Radiat. Res.*, 175 :57-65, 2011.
Nelson, In : *Thousands of New Cancers Predicted Due to Increased use of CT*, Medscape, 2009.
Oberley and Spitz, In: *Methods in Enzymology*, Packer (Ed.), Academic Press, 105:457-469, 1984.
Oka et al., *Organic Letters* 11(4):967-970, 2009.
Rothkamm et al., *Radiology*, 242:244-251, 2007.
Saynak et al., *Cancer Therapy*, 4: 283-288, 2006.
Semelka et al., *J. Magn. Reason. Imaging*, 25(5) :900-909, 2007.
Sigurdson et al., *Cancer Res.*, 68(21) :8825-8831, 2008.
Smith et al., *Health Phys.*, 85(1):23-29, 2003.
Srinivasan et al., *Int. J. Radiat. Biol.*, 78 :535-543, 2002.
Tucker and Luckinbill, *Radiat. Res.*, 175(5):631-637, 2011.
Yu et al., *Imaging Med.*, 1(1): 65-84, 2009.

\* cited by examiner

METHODS AND COMPOSITIONS FOR PROTECTION OF CELLS AND TISSUES FROM COMPUTED TOMOGRAPHY RADIATION

CROSS-REFERENCE TO RELATED APPLICATIONS

This application is a continuation of U.S. patent application Ser. No. 13/822,223 filed Apr. 22, 2013, which is a national phase application under 35 U.S.C. § 371 of International Application No. PCT/US2011/051946 filed Sep. 16, 2011, which claims the benefit of the filing date of U.S. Provisional Application Ser. No. 61/383,592 filed Sep. 16, 2010. The entire contents of each of the above-referenced disclosures are specifically incorporated herein by reference without disclaimer.

STATEMENT OF GOVERNMENT INTEREST

This invention was made in part with government support under Grant No. DE-FG02-05ER64086 from the Department of Energy. The United States Government has certain rights in the invention.

BACKGROUND OF THE INVENTION

I. Field of the Invention

The invention is generally related to biochemistry, physiology, medicine, and the inhibition of genomic instability caused by ionizing radiation, such as computed tomography imaging.

II. Background

Computed tomography (CT) is a powerful medical imaging method employing tomography created by computer processing. However, CT scans have been estimated to produce non-negligible increases in the probability of lifetime cancer mortality, leading to calls for the use of reduced current settings for CT scans. Estimated lifetime cancer mortality risks attributable to the radiation exposure from a CT in a 1-year-old are 0.18% (abdominal) and 0.07% (head)—an order of magnitude higher than for adults—although those figures still represent a small increase in cancer mortality over the background rate. In the United States, of approximately 600,000 abdominal and head CT examinations annually performed in children under the age of 15 years, a rough estimate is that 500 of these individuals might ultimately die from cancer attributable to the CT radiation. The additional risk is still very low (0.35%) compared to the background risk of dying from cancer (23%). However, if these statistics are extrapolated to the current number of CT scans, the additional rise in cancer mortality could be 1.5 to 2%. Furthermore, certain conditions can require children to be exposed to multiple CT scans. Again, these calculations can be problematic because the assumptions underlying them could overestimate the risk.

In 2009 a number of studies appeared that further defined the risk of cancer that may be caused by CT scans (Brenner et al., 2001) One study indicated that radiation by CT scans is often higher and more variable than cited and each of the 19,500 CT scans that are daily performed in the U.S. is equivalent to 30 to 442 chest x-rays in radiation. It has been estimated that CT radiation exposure will result in 29,000 new cancer cases just from the CT scans performed in 2007 (Brenner et al., 2001). The most common cancers caused by CT are thought to be lung cancer, colon cancer and leukemia with younger people and women more at risk. Although CT scans come with an additional risk of cancer (it can be estimated that the radiation exposure from a full body scan is the same as standing 2.4 km away from the WWII atomic bomb blasts in Japan (Nelson, 2009; Semelka et al., 2007), especially in children, the benefits that stem from their use outweighs the risk in many cases (Khamsi, 2007). A number of vitamins and nutritional supplements have been shown to protect the organism when it is exposed to ionizing radiation. However, improved methods for consistently and reproducibly reducing the risk of CT associated radiation are needed.

SUMMARY OF THE INVENTION

Thus, in accordance with the disclosure, compositions and methods are provided for protection of cells and tissue from damaging effects of computer tomorgraphy radiation. In some embodiments, there are methods of inhibiting genomic instability in a subject caused by diagnostic radiology procedures that involve exposure to ionizing radiation. In specific embodiments, methods comprise administering to the subject an effective dose of a phosphorothioate compound prior to and/or following exposure to a diagnostic radiology procedure, including, but not limited to a lower gastrointestinal (GI) series, which is a medical procedure that involves taking X-ray pictures and which is also called a barium enema. In certain embodiments, methods specifically exclude the use of conventional X-ray imaging that does not involve computed tomography.

In certain aspects, methods include inhibiting genomic instability in a subject caused by computed tomography (CT) scan radiation comprising administering to the subject an effective dose of a phosphorothioate compound prior to and/or following exposure to the CT scan radiation. The dose may provide a blood level of about 1 to 150 µM. The CT radiation dose may be about 1-25 cGy, or about 1-10 cGy. In other embodiments, the CT radiation dose may be about, at least about, or at most about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000 (and any range derivable therein). In certain embodiments, the CT radiation dosage is not lower than about 20, 30, 40, 50, 60, 70, 80, 90, 100, 110, 120, 130, 140, or 150 millirems. In further embodiments, the CT radiation dose may be about, at least about, or at most about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, or 20.0 mSv, or any range derivable therein.

Inhibiting genomic instability may comprise reducing micronuclei formation and/or hyper-recombination. The method may further comprise administering to the subject a second protective agent, such as vitamin E, selenium or catalase.

The phosphorothioate may be administered prior to exposure to the CT scan radiation, or at the time of, or up to one hour following exposure to the CT scan radiation. The phosphorothioate may also be provided both before and after the CT scan. The phosphorothioate may be administered subcutaneously, such as by the subject using an auto-injector device. The phosphorothioate may be administered intravenously, topically or orally.

The subject may have cancer or may be suspected of having cancer. The subject may have had 1, 2 or 3 previous CT scans. The subject may be a human or a non-human animal.

Also provided are methods of assessing a subject with computed tomography (CT) scan radiation comprising (a) administering to the subject an effective dose of a phosphorothioate compound prior to and/or immediately or 1 hour following exposure to the CT scan radiation; and (b) subjecting the subject to a CT scan.

Another embodiment comprises a method of diagnosing cancer in a subject using computed tomography (CT) scan radiation dose comprising (a) administering to the subject an effective dose of a phosphorothioate compound prior to and/or immediately or 1 hr following exposure to the CT scan radiation; and (b) subjecting the subject to a CT scan.

A further embodiment involves a method of assessing the treatment of cancer in a subject using computed tomography (CT) scan radiation comprising administering to the subject an effective dose of a phosphorothioate compound prior to and/or immediately following exposure to the CT scan radiation; (b) treating the subject with an anti-cancer therapy; and (c) subjecting the subject to a CT scan. The CT scan may be compared to a pre-treatment CT scan of the subject.

Also provided is a method for modulating mitochondrial superoxide dismutase 2 (SOD2) levels in a subject comprising administering to the subject an effective dose of a phosphorothioate compound prior to and/or following exposure to the CT scan radiation.

Phosphorothioates used in the inventive methods are exemplified by, not limited to S-2-(3-aminopropylamino) ethyl phosphorothioic acid (amifostine, WR-2721), 2-[(aminopropyl)amino]ethanethiol (WR-1065), S-1-(aminoethyl) phosphorothioc acid (WR-638), S-[2-(3-methylaminopropyl)aminoethyl]phosphorothioate acid (WR-3689), S-2-(4-aminobutylamino) ethylphosphorothioic acid (WR-2822), 3-[(2-mercapto ethyl)amino]propionamide p-toluenesulfonate (WR-2529), S-1-(2-hydroxy-3-amino) propyl phosphorothioic acid (WR-77913), 2-[3-(methylamino) propylamino] ethanethiol (WR-255591), S-2-(5-aminopentylamino) ethyl phosphorothioic acid (WR-2823), [2-[(aminopropyl) amino] ethanethiol] N,N,'-dithiodi-2,1-(ethanediyl) bis-1,3-propanediamine (WR-33278),1-[3-(3-aminopropyl) thiazolidin-2-Y1]-D-gluco-1,2,3,4,5 pentane-pentol dihydrochloride (WR-255709), 3-(3-methylaminopropylamino) propanethiol dihydrochloride (WR-151326), S-3-(3-methylaminopropylamino) propyl phosphorothioic acid (WR-151327), a prodrug or salt thereof. In particular aspects, the phosphorothioate is WR-2721.

Phosphorothioate can be provided at a dose of at least about, at most about, or about 0.1, 0.5, 1, 2, 3, 4, 5, 6, 7, 8, 9, 10, 25, 50, 100, 200, 400 mg/kg, or mg/kg/day, including all values or ranges there between. In certain aspects a phosphorothioate is administered at a dose of at least about, at most about, or about 20 mg/kg to about 200 mg/kg, and more particularly about 75 mg/kg or mg/kg/day. Phosphorothioate can be administered 1, 2, 3, 4, 5, or more times a day, a week, a month, or a year. In certain aspects, a phosphorothioate is administered about every 24, 48, 72, 96, 120 hours or any range derivable therein. The phosphorothioate may be provided intravenously, i.v., but also methods may include administration via other enteral routes—oral, intra-arterial, subcutaneous, intraperitoneal injection, infusion or perfusion—or via inhalation routes.

In certain embodiments, the phosphorothioate may be provided within, before, or after 10, 15, 20, 25, 30, 35, 40, 45, 50, 55, 60, 65, 70, 75, 80, 85, 90, 95, 100, 110, 120, 130, 140, 150, 160, 170, 180 190, 200, 210, 220, 230, 240, 250, 260, 270, 280, 290, or 300 minutes (or any range derivable therein) being exposed to CT radiation. In certain embodiments, the subject is exposed to CT radiation Methods may further involve administering intravenously to the subject a contrast agent, which is used to visualize a CT scan.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The terms "inhibiting," "reducing," or "prevention," or any variation of these terms, when used in the claims and/or the specification includes any measurable decrease or complete inhibition to achieve a desired result. The use of the word "a" or "an" when used in conjunction with the term "comprising" in the claims and/or the specification may mean "one," but it is also consistent with the meaning of "one or more," "at least one," and "one or more than one." Throughout this application, the term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1—Representative photomicrographs of GFP+/− colonies displaying delayed hyperrecombination.

DETAILED DESCRIPTION OF THE INVENTION

Figure 1:
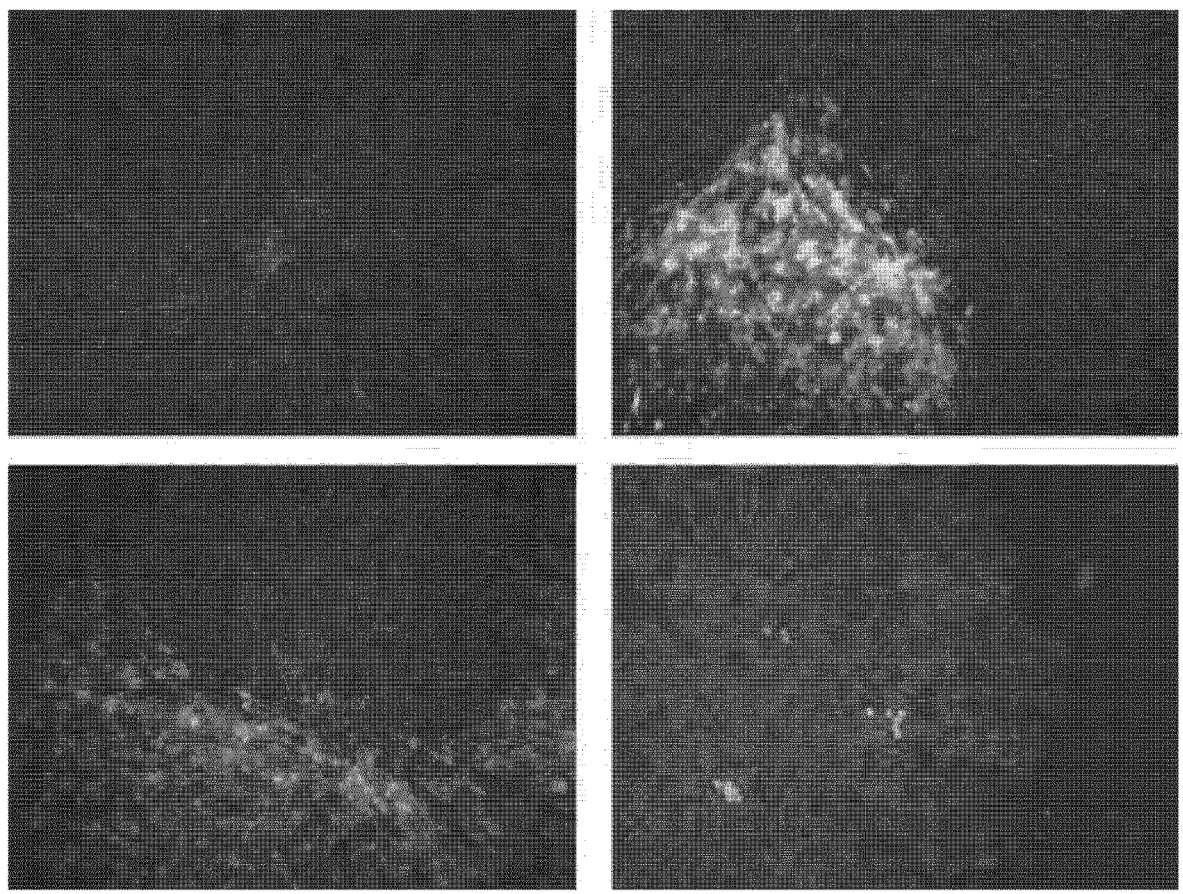

Diagnostic radiology currently uses computed tomograpy, or "CT" scanning technology as a main diagnostic tool. Seventy-two million CT scans were performed in the USA alone in 2007. Unfortunately, epidemology studies predict that CT-related radiation will lead to 29,000 new cancers each year. A typical CT scan results in organ doses 100 times larger than chest X-rays. People who have a CT scan for a medical issue generally have on the average 2 to 3 scans. Children are the most susceptible to the carcinogenic effect of CT scans. The entire radiation dose range utilized in CT scans are of the magnitude demonstrated from the Atomic Bomb Survivors Data to significantly elevate carcinogenic risk above background levels. Thus, there is a need for a method/product to reduce these risks thus making CT scans safer for the general population and specifically children.

Here, amifostine is shown at radiation doses typical of CT scans, e.g., 10 cGy, to be effective in protecting against hyper-recombination cellular processes, an important element in the development of genomic instability and eventual cancer development and readily observed in the low radiation dose range utilized by CT scans. Furthermore, amifostine has been demonstrated to protect against micronuclei formation in irradiated cells even when administered up to one hour following irradiation. This is a much more toxic genomic instability endpoint than mutagenesis since mutations occur at the gene level while micronuclei formation represent whole scale chromosomal damage resulting in the loss of parts of chromosomes.

It is therefore proposed that amifostine and other phosphorotioates can be used to reduce the serious side effects of diagnostic radiology CT scans, namely, the induction of genomic instability characterized by hyper recombination induced by low doses of radiation that leads to gross but non-lethal chromosomal damage as evidenced by micronuclei formation that can culminate in cancer development. It must be stressed that alteration of the normal background recombination processes that occur in unirradiated cells induced by irradiation result in delayed deleterious effects in which the intregrety of the genome is negatively affected through hyper, eg, significantly elevated, recombination processes. Each recombination event carries with it a probability of incorrect rejoining and hence the introduction of delayed DNA damage. Hyper recombination is a manifestation of loss of genomic homeostasis and elevated probability of genomic damage. Malignancies arise as a consequence of acquired genetic change as evidenced by genomic instability in cells capable of clonal expansion. Conventional wisdom holds that the induction of genomic instability as evidenced by hyper recombination is an early marker that can be directly observed at very low doses of radiation and may represent the first critical step in the generation of radiation-induced cancers. Thus, this method involves the use of phosphorothioates such as amifostine for the purpose of protecting against diagnostic radiation level doses of radiation when administered either 30 min before or 1 h following irradiation. It is proposed that such agents will advantageously be administered subcutaneously using a self injector apparatus, optionally with a second cytoprotective agent.

I. COMPUTED TOMOGRAPHY (CT) SCANNING

Computed tomography (CT) is a medical imaging method employing tomography created by computer processing. Contrast enhancing agents are routinely used and these in turn can exacerbate radiation damage to the cellular DNA by virtue of their high Z atomic numbers which facilitate the intensity of the scattered radiation and thus improve the measured image. Such contrast agents have, therefore, as a side effect the ability to further sensitize the cells to the genomic damaging properties of the radiation doses used in acquiring CT images. Digital geometry processing is used to generate a three-dimensional image of the inside of an object from a large series of two-dimensional X-ray images taken around a single axis of rotation.

CT produces a volume of data which can be manipulated, through a process known as "windowing," in order to demonstrate various bodily structures based on their ability to block the X-ray beam. Although historically the images generated were in the axial or transverse plane, orthogonal to the long axis of the body, modern scanners allow this volume of data to be reformatted in various planes or even as volumetric (3D) representations of structures. Although most common in medicine, CT is also used in other fields, such as non-destructive materials testing. Usage of CT has increased dramatically over the last two decades—an estimated 72 million scans were performed in the United States in 2007.

Digital tomosynthesis combines digital image capture and processing with simple tube/detector motion as used in conventional radiographic tomography. Although there are some similarities to CT, it is a separate technique. In CT, the source/detector makes a complete 360-degree rotation about the subject obtaining a complete set of data from which images may be reconstructed. In digital tomosynthesis, only a small rotation angle (e.g., 40 degrees) with a small number of discrete exposures (e.g., 10) are used. This incomplete set of data can be digitally processed to yield images similar to conventional tomography with a limited depth of field. However, because the image processing is digital, a series of slices at different depths and with different thicknesses can be reconstructed from the same acquisition, saving both time and radiation exposure.

Because the data acquired is incomplete, tomosynthesis is unable to offer the extremely narrow slice widths that CT offers. However, higher resolution detectors can be used, allowing very-high in-plane resolution, even if the Z-axis resolution is poor. The primary interest in tomosynthesis is in breast imaging, as an extension to mammography, where it may offer better detection rates with little extra increase in radiation exposure.

Reconstruction algorithms for tomosynthesis are significantly different from conventional CT, because the conventional filtered back projection algorithm requires a complete set of data. Iterative algorithms based upon expectation maximization are most commonly used, but are extremely computationally intensive. Some manufacturers have produced practical systems using off-the-shelf GPUs to perform the reconstruction.

Since its introduction in the 1970s, CT has become an important tool in medical imaging to supplement X-rays and medical ultrasonography. It has more recently been used for preventive medicine or screening for disease, for example CT colonography for patients with a high risk of colon cancer, or full-motion heart scans for patients with high risk of heart disease. A number of institutions offer full-body scans for the general population. However, this is a controversial practice, given its lack of proven benefit, cost, radiation exposure, and the risk of finding 'incidental' abnormalities that may trigger additional investigations. The increased use of CT scans has been the greatest in two fields: screening of adults (screening CT of the lung in smokers, virtual colonoscopy, CT cardiac screening and whole-body CT in asymptomatic patients) and CT imaging of children. Shortening of the scanning time to around 1 second, eliminating the strict need for subject to remain still or be sedated, is one of the main reasons for large increase in the pediatric population (especially for the diagnosis of appendicitis).

| TYPICAL SCAN DOSES | | |
| --- | --- | --- |
| Examination | Typical effective dose (mSv) | (millirem) |
| Chest X-ray | 0.1 | 10 |
| Head CT | 1.5 | 150 |
| Screening mammography | 3 | 300 |
| Abdomen CT | 5.3 | 530 |
| Chest CT | 5.8 | 580 |
| CT colonography | 3.6-8.8 | 360-880 |
| Chest, abdomen and pelvis CT | 9.9 | 990 |
| Cardiac CT angiogram | 6.7-13 | 670-1300 |
| Barium enema | 15 | 1500 |
| Neonatal abdominal CT | 20 | 2000 |

For purposes of comparison, the average background exposure in the UK is 1-3 mSv per year.

Because contrast CT scans rely on intravenously administered contrast agents in order to provide superior image quality, there is a low but non-negligible level of risk associated with the contrast agents themselves. Many patients report nausea and discomfort, including warmth in the crotch which mimics the sensation of wetting oneself. Certain patients may experience severe and potentially life-threatening allergic reactions to the contrast dye.

The contrast agent may also induce kidney damage. The risk of this is increased with patients who have preexisting renal insufficiency, preexisting diabetes, or reduced intravascular volume. In general, if a patient has normal kidney function, then the risks of contrast nephropathy are negligible. Patients with mild kidney impairment are usually advised to ensure full hydration for several hours before and after the injection. For moderate kidney failure, the use of iodinated contrast should be avoided; this may mean using an alternative technique instead of CT, e.g., MM. Paradoxically, patients with severe renal failure requiring dialysis do not require special precautions, as their kidneys have so little function remaining that any further damage would not be noticeable and the dialysis will remove the contrast agent.

An important issue within radiology today is how to reduce the radiation dose during CT examinations without compromising the image quality. Generally, higher radiation doses result in higher-resolution images, while lower doses lead to increased image noise and unsharp images. Increased dosage raises the risk of radiation induced cancer—a four-phase abdominal CT gives the same radiation dose as 300 chest x-rays. Several methods exist which can reduce the exposure to ionizing radiation during a CT scan.

New software technology can significantly reduce the required radiation dose. The software works as a filter that reduces random noise and enhances structures. In this way, it is possible to get high-quality images and at the same time lower the dose by as much as 30 to 70%. Other suggestions are to individualize the examination and adjust the radiation dose to the body type and body organ examined (different body types and organs require different amounts of radiation), and, prior to every CT examination, evaluate the appropriateness of the exam whether it is motivated or if another type of examination is more suitable (higher resolution is not always suitable for any given scenario, such as detection of small pulmonary masses).

X-ray slice data is generated using an X-ray source that rotates around the object; X-ray sensors are positioned on the opposite side of the circle from the X-ray source. The earliest sensors were scintillation detectors, with photomultiplier tubes excited by (typically) cesium iodide crystals. Cesium iodide was replaced during the 1980s by ion chambers containing high pressure Xenon gas. These systems were in turn replaced by scintillation systems based on photo diodes instead of photomultipliers and modern scintillation materials with more desirable characteristics. Many data scans are progressively taken as the object is gradually passed through the gantry.

Newer machines with faster computer systems and newer software strategies can process not only individual cross sections but continuously changing cross sections as the gantry, with the object to be imaged, is slowly and smoothly slid through the X-ray circle. These are called helical or spiral CT machines. Their computer systems integrate the data of the moving individual slices to generate three dimensional volumetric information (3D-CT scan), in turn viewable from multiple different perspectives on attached CT workstation monitors. This type of data acquisition requires enormous processing power, as the data are arriving in a continuous stream and must be processed in real-time.

In conventional CT machines, an X-ray tube and detector are physically rotated behind a circular shroud (see the image above right); in the electron beam tomography (EBT) the tube is far larger and higher power to support the high temporal resolution. The electron beam is deflected in a hollow funnel-shaped vacuum chamber. X-rays are generated when the beam hits the stationary target. The detector is also stationary. This arrangement can result in very fast scans, but is extremely expensive.

CT is used in medicine as a diagnostic tool and as a guide for interventional procedures. Sometimes contrast materials such as intravenous iodinated contrast are used. This is useful to highlight structures such as blood vessels that otherwise would be difficult to delineate from their surroundings. Using contrast material can also help to obtain functional information about tissues.

Once the scan data has been acquired, the data must be processed using a form of tomographic reconstruction, which produces a series of cross-sectional images. The most common technique in general use is filtered back projection, which is straight-forward to implement and can be computed rapidly. However, this is not the only technique available: the original EMI scanner solved the tomographic reconstruction problem by linear algebra, but this approach was limited by its high computational complexity, especially given the computer technology available at the time. More recently, manufacturers have developed iterative physical model-based expectation-maximization techniques. These techniques are advantageous because they use an internal model of the scanner's physical properties and of the physical laws of X-ray interactions. By contrast, earlier methods have assumed a perfect scanner and highly simplified physics, which leads to a number of artifacts and reduced resolution—the result is images with improved resolution, reduced noise and fewer artifacts, as well as the ability to greatly reduce the radiation dose in certain circumstances. The disadvantage is a very high computational requirement, which is at the limits of practicality for current scan protocols.

Pixels in an image obtained by CT scanning are displayed in terms of relative radiodensity. The pixel itself is displayed according to the mean attenuation of the tissue(s) that it corresponds to on a scale from +3071 (most attenuating) to −1024 (least attenuating) on the Hounsfield scale. Pixel is a two dimensional unit based on the matrix size and the field of view. When the CT slice thickness is also factored in, the unit is known as a Voxel, which is a three dimensional unit. The phenomenon that one part of the detector cannot differentiate between different tissues is called the "Partial Volume Effect." That means that a big amount of cartilage and a thin layer of compact bone can cause the same attenuation in a voxel as hyperdense cartilage alone. Water has an attenuation of 0 Hounsfield units (HU) while air is −1000 HU, cancellous bone is typically +400 HU, cranial bone can reach 2000 HU or more (os temporale) and can cause artifacts. The attenuation of metallic implants depends on atomic number of the element used: Titanium usually has an amount of +1000 HU, iron steel can completely extinguish the X-ray and is therefore responsible for well-known line-artifacts in computed tomograms. Artifacts are caused by abrupt transitions between low- and high-density materials, which results in data values that exceed the dynamic range of the processing electronics.

II. GENOMIC INSTABILITY AND CYTOPROTECTION

A. Genomic Instability

Genomic instability can be defined as an increased rate of genetic alterations in the genome of the progeny of irradiated cells multiple generations after the initial insult such as chromosomal rearrangements and aberrations, micronuclei formation, gene mutations, microsatellite instability, changes in ploidy, and decreased plating efficiency (PE) (Morgan, 2003a; Morgan, 2003b) with an association between chromosomal instability and delayed reproductive cell death (Limoli et al., 1997; Marder and Morgan, 1993).

Micronuclei are small nuclei that forms whenever a chromosome or a fragment of a chromosome is not incorporated into one of the daughter nuclei during cell division. In newly formed red blood cells in humans, these are known as Howell-Jolly bodies. The can result from genomic toxicity, such as that caused by radiation. Indeed, micronuclei formation represents a significantly greater level of chromosomal damage than what is associated with mutagenesis, which is gene specific.

Normal recombination processes occur in cells as a means to preserve genomic integrity and maintain genomic stability. The frequency of these processes can be negatively affected by stress inducing agents such as ionizing radiation. The subsequent elevation of recombinative frequencies in cells leads to a higher probability of errors and increased DNA damage long after the initial radiation exposure. In contrast to major deleterious events induced by high doses of radiation exposure such as loss of cell viability, mutagenesis, chromosomal and DNA strand breaks, this deleterious process with its downstream carcinogenic consequence can be observed and measured at relatively low doses of radiation in the range used routinely for CT scans. It must be stressed that the consequences of hyperrecombination are not limited to mutagenesis but also encompass the potential of gene augmentation due to hyper duplication and relocation within the genome thus affecting a myriad of genomic processes including the possibility of epigenetic processes such as gene silencing.

Gene conversion can produce a local loss of heterozygosity (LOH) as well as deletions and inversions at linked repeats and translocations (Nickoloff, 2002). The inventor has utilized a green fluorescence protein (GFP)-based assay using human RKO-derived cells to study the role of delayed hyper-recombination in radiation-induced genomic instability (Huang et al., 2004). A GFP direct repeat homologous recombination substrate is incorporated in RKO cells. One copy is driven by the CMV promoter but is inactivated by an XhoI linker frame shift mutation, and the second copy has a wild-type coding capacity but is inactive because it lacks a promoter.

Genomic instability can be measured by analysis of delayed hyperrecombination and mutation/deletion at the GFP direct repeat substrate. GFP-RKO cells can be GFP− or GFP+. When these cells are plated, colonies arising from single cells are either homogenously colorless (GFP−) or green (GFP+). A GFP− cell can convert to a GFP+ cell directly by radiation-induced delayed hyperrecombination. Similarly, a GFP+ cell can be converted to a GFP− cell directly by a radiation-induced point mutation or deletion (see FIG. 1). Mixed colonies arise by delayed hyperrecombination and can easily be scored using the criteria of having at least >4 cells per colony having an altered fluorescent phenotype. The frequency of induced instability can be calculated as the number of GFP+/− colonies per total surviving colonies scored.

Radiation exposure can induce delayed hyper-recombination with up to 10% of the cells producing mixed GFP+/− colonies. Cells displaying delayed hyperrecombination show no evidence of delayed reproductive cell death and there is no correlation between delayed chromosomal instability and delayed hyperrecombination, indicating that these forms of genome instability arise by distinct mechanisms. The inclusion of radiation-induced delayed hyperrecombination as an important endpoint of genomic instability and the focus of low dose radiation studies reflects three important elements thought to be important in the carcinogenic risk process. First, genome instability associated with delayed hyperrecombination increases the probability of uncovering recessive mutations via LOH. Second, delayed hyperrecombination can be induced by doses of radiation that cause little or no cytotoxicity, thus increasing the relative fraction of cells at risk and allowing them to survive and accumulate mutations necessary for immortalization and cellular transformation. And third, because delayed hyperrecombination is important for the repair of DNA double-strand breaks, cells with a hyperrecombination phenotype may display enhanced resistance to radiation.

B. Cytoprotection

Cytoprotection is the use of a chemical agent to prevent cell killing and/or loss of function in normal tissues exposed to a deleterious extracellular or intracellular environment, such as radiation. Amifostine is such a cytoprotective agent, but has been used in a limited fashion due to early studies with animal models. The present invention seeks, in one embodiment, to protect cells from radiation associated with CT scans.

Evidence of cytoprotection in vivo can also be measured by analysis of certain biomarkers related to genetic instabilities. For example, chromosome translocation frequencies have been noted as the hallmark of exposure to ionizing radiation and have been utilized to detect chromosomal damage from diagnositic X-rays at the 50 mGy level. See Tucker and Luckinbill, *Radiat Res.* 2011, 175(5), 631-7; Bhatti et al., *Radiat. Environ. Biophys.* 2010, 49(4), 685-692; and Sigurdson et al., *Cancer Res.* 2008, 68(21), 8825-8831, each of which are hereby incorporated by reference in their entirety.

In another example, cytoprotection in vivo can also be measured by analysis of micronuclei formation. See Kim et al., *Cancer Res.* 2006, 66, 10377-10383, which is hereby incorporated by reference in its entirety. Micronuclei are formed from either chromosome fragments or whole chromosomes that lag behind at anaphase during cell division, and their formation is considered to be an important biomarker for genotixicity testing. In particular, micronuclei have been shown to be generated at low radiation dosage levels (e.g., 10 cGy). See Murley et al., *Radiat. Res.,* 175:57-65, 2011, which is hereby incorporated by reference in its entirety.

Evidence of cytoprotection ex vivo can also be measured by analysis of radiation-induced histone H2AX phosphorylation at serine 139 (γ-H2AX). It has been shown that quantity of γ-H2AX-positive cells increase with increasing radiation dose, with a dose- and time-dependent decay. γ-H2AX formation in irradiated cells, as a function of relative DNA content, can be quantified by bivariant flow cytometry analysis with FITC-conjugated γ-H2AX antibody and nuclear DAPI staining; measurement can be made after about 1 hour after cellular exposure to ionizing radiation. See, Kataoka et al., *Radiat. Res.* 2007, 168, 106-114, which is hereby incorporated by reference in its entirety. In particular, γH2AX-based visualization and quantification of DNA damage induced in peripheral blood mononuclear cells (PBMCs) can be used to estimate the radiation dose received by adult patients who undergo multidetector computed tomography (CT), and has been used to detect dose as low as 6.3 mGy. See Rothkamm et al., *Radiology* 2007, 242, 244-251, which is hereby incorporated by reference in its entirety.

In another example, evidence of cytoprotection ex vivo can also be measured by analysis of mutant frequency at the hypoxanthine-guanine phosphoribosyltransferase (HPRT) locus, for example, in human G(0) peripheral blood lymphocytes. See Kumar et al., *Radiat Res.* 2006, 165(1), 43-50, which is hereby incorporated by reference in its entirety. HPRT mutant frequency in lymphocytes has been successfully utilized to estimate average dose of 9.5 cGy for Russian Chernobyl cleanup workers based on the average increase in translocation frequency. See Jones et al., *Radiat Res.* 2002, 158(4), 424-42, which is hereby incorporated by reference in its entirety.

In another embodiment, one may combine the use of phosphorothioate protection with a second cytoprotective strategy. A description of cytoprotection and methods of assaying for cytoprotection as it relates to cancer therapies are provided in U.S. Pat. Nos. 5,567,686; 5,488,042, 5,891, 856, and 5,869,338. Any of the cytoprotective therapies described therein may be combined with the phosphorothioate treatments of the present invention.

III. PHARMACEUTICAL COMPOSITIONS AND ROUTES OF ADMINISTRATION

A. Phosphorothioates

A general description of the class of compounds and their properties described in this application can be found in Sweeney, 1979 and Giambarresi and Jacobs, 1987, both of which are incorporated by reference. Compounds and designations exemplary of the class of phosphorothioates include S-2-(3-aminopropylamino)ethyl phosphorothioic acid (amifostine, WR-2721), 2-[(aminopropyl)amino]ethanethiol (WR-1065), S-1-(aminoethyl) phosphorothioc acid (WR-638), S-[2-(3-methylaminopropyl)aminoethyl]phosphorothioate acid (WR-3689), S-2-(4-aminobutylamino) ethylphosphorothioic acid (WR-2822), 3-[(2-mercapto ethyl)amino]propionamide p-toluenesulfonate (WR-2529), S-1-(2-hydroxy-3-amino)propyl phosphorothioic acid (WR-77913), 2-[3-(methylamino)propylamino]ethanethiol (WR-255591), S-2-(5-aminopentylamino)ethyl phosphorothioic acid (WR-2823), [2-[(aminopropyl)amino]ethanethiol]N, N,'-dithiodi-2,1-(ethanediyl)bis-1,3-propanediamine (WR-33278),1-[3-(3-aminopropyl)thiazolidin-2-Y1]-D-gluco-1, 2,3,4,5 pentane-pentol dihydrochloride (WR-255709), 3-(3-methylaminopropylamino)propanethiol dihydrochloride (WR-151326), and S-3-(3-methylaminopropylamino)propyl phosphorothioic acid (WR-151327).

B. Formulations and Routes of Administration

The compounds useful in the methods of the invention may be in the form of free acids, free bases, or pharmaceutically acceptable addition salts thereof. Such salts can be readily prepared by treating the compounds with an appropriate acid. Such acids include, by way of example and not limitation, inorganic acids such as hydrohalic acids (hydrochloric, hydrobromic, hydrofluoric, etc.), sulfuric acid, nitric acid, and phosphoric acid, and organic acids such as acetic acid, propanoic acid, 2-hydroxyacetic acid, 2-hydroxypropanoic acid, 2-oxopropanoic acid, propandioic acid, and butandioic acid. Conversely, the salt can be converted into the free base form by treatment with alkali.

Aqueous compositions of the present invention comprise an effective amount of the therapeutic compound, further dispersed in pharmaceutically acceptable carrier or aqueous medium. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof, and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain at least about, at most about, or about 1, 5, 10, 25, 50 mg or up to about 100 mg of human serum albumin per milliliter of phosphate buffered saline. Other pharmaceutically acceptable carriers include aqueous solutions, non toxic excipients, including salts, preservatives, buffers and the like.

A particular form of administration is the use of an auto-injector that can be pre-loaded with a "unit dose" (see below), or calibrated to reliably and/or repeatably deliver a unit dose of phosphorothioate. Most autoinjectors are spring-loaded syringes. By design, autoinjectors are easy to use and are intended for self-administration by patients, or administration by untrained personnel. The site of injection depends on the drug loaded, but it typically is administered into the thigh or the buttocks. The injectors were initially designed to overcome the hesitation associated with self-administration of the needle-based drug delivery device.

The autoinjector keeps the needle tip shielded prior to injection and also has a passive safety mechanism to prevent accidental firing (injection). Injection depth can be adjustable or fixed and a function for needle shield removal may be incorporated. Just by pressing a button, the syringe needle is automatically inserted and the drug is delivered. Once the injection is completed some auto injectors have visual indication to confirm that the full dose has been delivered. Autoinjectors contain glass syringes, this can make them fragile and contamination can occur. More recently companies have been looking into making autoinjectors syringes out of plastic to prevent this issue. Anapen®, EpiPens®, or the recently introduced Twinject®, are often prescribed to people who are at risk for anaphylaxis. Rebiject® and Rebiject® II autoinjectors are used for Rebif, the drug for interferon β-1a, used to treat Multiple Sclerosis. SureClick® autoinjector delivers a combination product for drugs Enbrel or Aranesp to treat arthritis or anemia, respectively. Any of these technologies could be adapted to deliver the compounds of the present invention.

Examples of non aqueous solvents include propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti oxidants, chelating agents and inert gases. The pH and exact concentration of the various components the pharmaceutical composition are adjusted according to well known parameters.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. Volume of an aerosol is typically between about 0.01 mL and 0.5 mL.

Additional formulations may be suitable for oral administration. "Oral administration" as used herein refers to any form of delivery of an agent or composition thereof to a subject wherein the agent or composition is placed in the mouth of the subject, whether or not the agent or composition is swallowed. Thus, oral 'administration' includes buccal and sublingual as well as esophageal administration. Absorption of the agent can occur in any part or parts of the gastrointestinal tract including the mouth, esophagus, stomach, duodenum, ileum and colon. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

In one embodiment, the oral formulation can comprise the phosphorothioates and one or more bulking agents. Suitable bulking agents are any such agent that is compatible with the phosphorothioates including, for example, lactose, microcrystalline cellulose, and non-reducing sugars, such as mannitol, xylitol, and sorbitol. One example of a suitable oral formulations includes spray-dried phosphorothioates-containing polymer nanoparticles (e.g., spray-dried poly(lactide-co-glycolide)/amifostine nanoparticles having a mean diameter of between about 150 nm and 450 nm; see, Pamujula, S. et a., *J. Pharmacy Pharmacol.* 2004, 56, 1119-1125, which is here by incorporated by reference in its entirety). The nanoparticles can contain between about 20 and 50 w/w % phosphorothioate; for example, between about 25% and 50%.

When the route is topical, the form may be a cream, ointment, salve or spray. Topical formulations may include solvents such as, but not limited to, dimethyl sulfoxide, water, N,N-dimethylformamide, propylene glycol, 2-pyrrolidone, methyl-2-pyrrolidone, and/or N-methylforamide. To enhance skin permeability, if necessary, the skin area to be treated can be pre-treated with dimethylsulfoxide; see Lamperti et al., *Radiation Res.* 1990, 124, 194-200, which is hereby incorporated by reference in its entirety.

In other embodiments, the therapeutic compositions may be for subcutaneous administration (e.g., injection and/or implantation). For example, implantable forms may be useful for patients which are expected to undergo multiple CT scans over an extended period of time (e.g., one week, two weeks, one month, etc.). In one example, such subcutaneous forms can comprise the phosphorothioates and a carrier, such as a polymer. The polymers may be suitable for immediate or extended release depending on the intended use. In one example, the phosphorothioate can be combined with a biodegradable polymer (e.g., polylactide, polyglycolide, and/or a copolymers thereof). In another example, subcutaneous forms can comprise a microencapsulated form of the phosphorothioate, see, e.g., Srinivasan et al., *Int. J. Radiat. Biol.* 2002, 78, 535-543, which is hereby incorporated by reference in its entirety. Such microencapsulated forms may comprise the phosphorothioate and one or more surfactant and other excipients (e.g., lactose, sellulose, cholesterol, and phosphate- and/or stearate-based surfactants).

In a further embodiment, the therapeutic compounds may be administered transdermally through the use of an adhesive patch that is placed on the skin to deliver the therapeutic compounds through the skin and into the bloodstream. An advantage of the transdermal drug delivery route relative to other delivery systems such as oral, topical, or intravenous is that the patch provides a controlled release of the therapeutic compound into the patient, usually through a porous membrane covering a reservoir of the therapeutic compound or through body heat melting thin layers of therapeutic compound embedded in the adhesive. In practicing this invention, any suitable transdermal patch system may be used including, without limitation, single-layer drug-in-adhesive, multi-layer drug-in-adhesive, and reservoir.

The therapeutic compositions may optionally further comprise a second protective agent. The second therapeutic agent can be an antioxidant. Examples of suitable antioxidants include, but are not limited to ascorbic acid (vitamin C), glutathione, lipoic acid, uric acid, β-carotene, lycopene, lutein, resveratrol, retinol (vitamin A), α-tocopherol (vitamin E), ubiquinol, selenium, and catalase. In certain embodiments, the second therapeutic agent is vitamin E, selenium or catalase.

An effective amount of the therapeutic composition is determined based on the intended goal, such as enhancing or extending the lifespan of a beta cell under hyperglycemic conditions. The term "unit dose" or "dosage" refers to physically discrete units suitable for use in a subject, each unit containing a predetermined quantity of the therapeutic composition calculated to produce the desired responses, discussed above, in association with its administration, i.e., the appropriate route and treatment regimen. The quantity to be administered, both according to number of treatments and unit dose, depends on the protection desired. An effective dose is understood to refer to an amount necessary to achieve a particular effect, for example, an increased antioxidant capability of a cell. In the practice of the present invention, it is contemplated that doses in the range from 10 mg/kg to 200 mg/kg can affect the protective capability of these compounds. Thus, it is contemplated that doses include doses of about 0.1, 0.5, 1, 5, 10, 15, 20, 25, 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, and 200 µg/kg or mg/kg. Furthermore, such doses can be administered at multiple times during a day, and/or on multiple days, weeks, or months.

In certain embodiments, the effective dose is one which can provide a blood level of about 1 µM to 150 µM. In another embodiment, the effective dose provides a blood level of about 4 µM to 100 µM; or about 1 µM to 100 µM; or about 1 µM to 50 µM; or about 1 µM to 40 µM; or about 1 µM to 30 µM; or about 1 µM to 20 µM; or about 1 µM to 10 µM; or about 10 µM to 150 µM; or about 10 µM to 100 µM; or about 10 µM to 50 µM; or about 25 µM to 150 µM; or about 25 µM to 100 µM; or about 25 µM to 50 µM; or about 50 µM to 150 µM; or about 50 µM to 100 µM. In other embodiments, the dose can provide the following blood level of the compound that results from a phosphorothioate compound being administered to a subject: about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µM or any range derivable therein. In certain embodiments, the phosphorothioate compound that is administered to a subject is metabolized in the body to a metabolized phosphorothioate compound, in which case the blood levels may refer to the amount of that compound. Alternatively, to the extent the phosphorothioate compound is not metabolized by a subject, the blood levels discussed herein may refer to the unmetabolized phosphorothioate compound.

In some embodiments, the timing of administration is relevant. One, 2, 3, 4, or 5 doses may be administered to the patient before the CT scan is started on the patient. In some embodiments, the pre-CT scan dose is administered at most 10, 20, 30, 40, 50, or 60 minutes (or any range derivable therein) before the start of the scan. In further embodiments, the pre-CT scan dose is administered at least 12, 18 or 24 hours (or any range derivable therein) before the start of the scan. In some embodiments, a dose is administered 10, 20, 30, 40, 50, or 60 minutes, or 1, 2, or 3 hours (or any range derivable therein) after the start of the scan or at the conclusion of the scan. In further embodiments, the post-CT scan dose is administered at least, up to, or at most 10, 20, 30, 40, 50, or 60 minutes, or up to 1, 2, or 3 hours (or any range derivable therein) after the start of the scan or at the conclusion of the scan. In certain embodiments, the dose is given only within 30 minutes, 1 hour, 1.5, 2, 2.5, or 3 hours (or any range derivable therein) within the start or end of the scan. Alternatively, in some embodiments the timing discussed herein may refer to the time at which the contrast agent is administered.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

It will be understood by those skilled in the art and made aware of this invention that dosage units of µg/kg or mg/kg of body weight can be converted and expressed in comparable concentration units of µg/ml or mM (blood levels), such as 4 µM to 100 µM. It is also understood that uptake is species and organ/tissue dependent. The applicable conversion factors and physiological assumptions to be made concerning uptake and concentration measurement are well-known and would permit those of skill in the art to convert one concentration measurement to another and make reasonable comparisons and conclusions regarding the doses, efficacies and results described herein.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention

Figure 2:
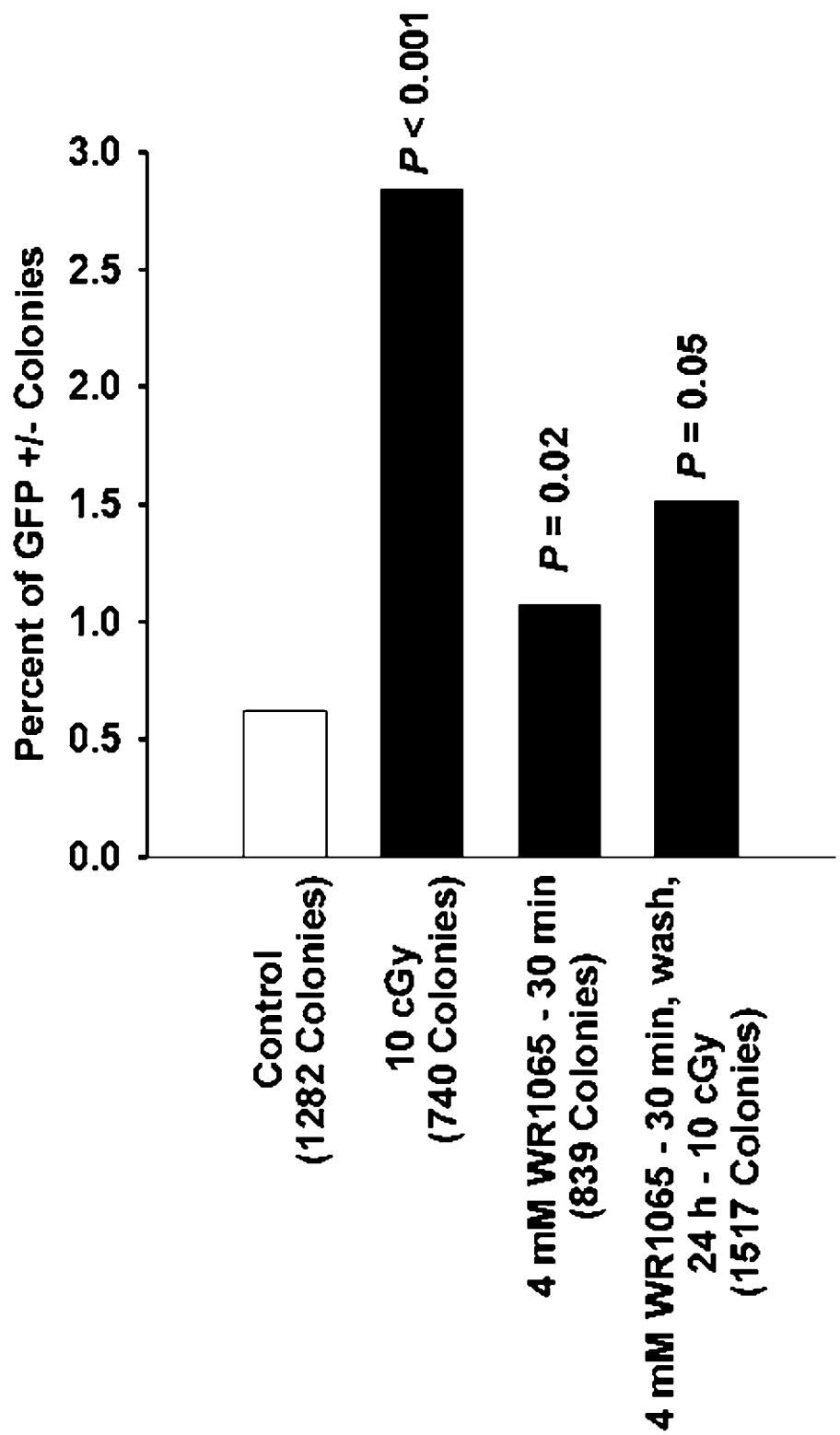
FIG. 2—Percentage of GFP+/− colonies as a function of treatment.
Figure 3:
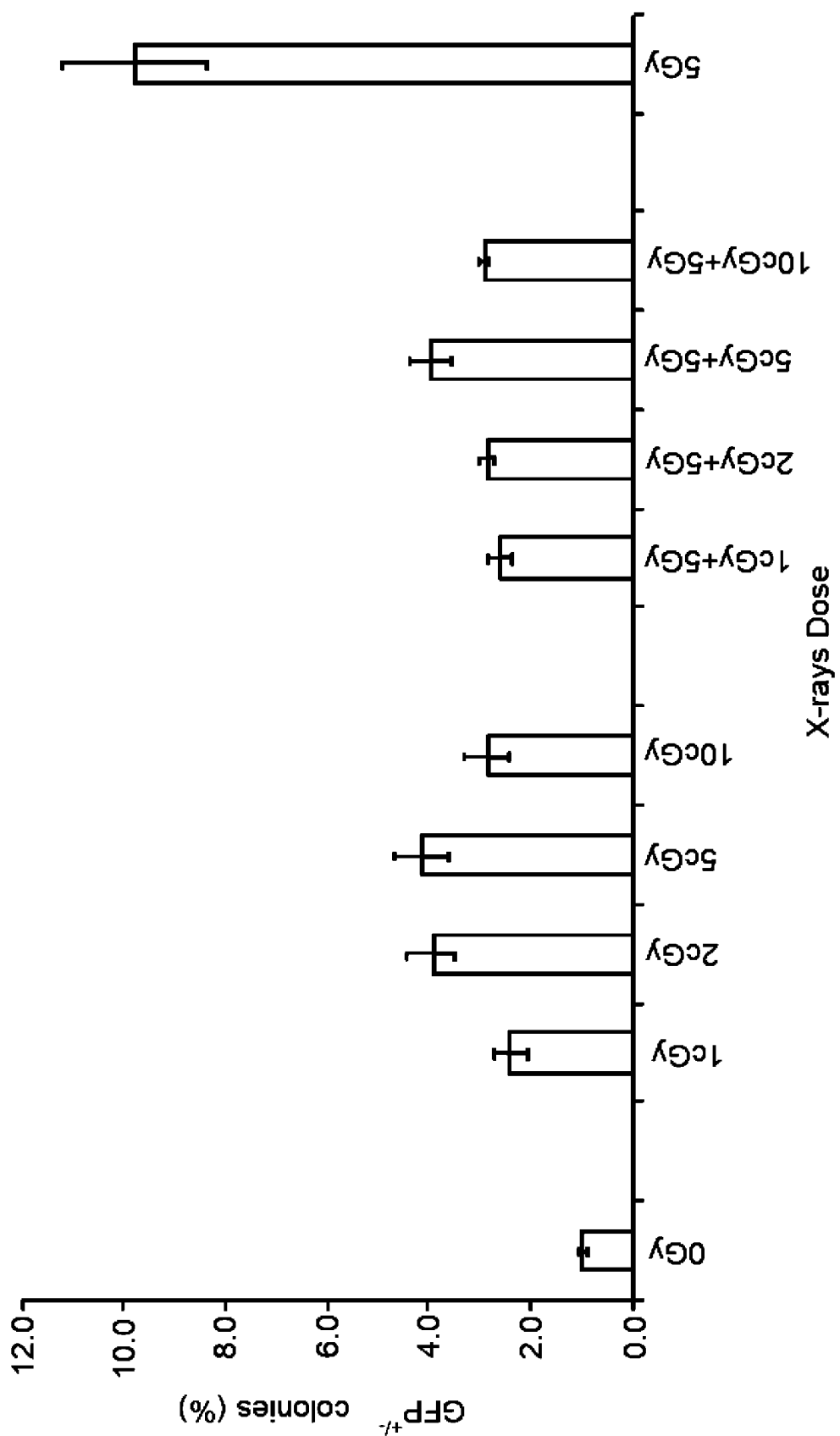
FIG. 3—Percentage of GFP+/− colonies as a function of treatment.

Example 1—Delayed Hyperrecombination Following Thiol Exposure Prior to Irradiation with 10 cGy Genomic instability was evaluated in RKO36 cells by analysis of delayed hyperrecombination and mutation/deletion at the GFP direct repeat substrate. All "pure" GFP+ or GFP− colonies reflect either a prior stable phenotype, or new, stable phenotype directly induced by radiation but if radiation induces a delayed instability at the GFP direct repeats, mixed GFP+/− colonies will form (see FIG. 1). Cells were exposed to 4 mM WR1065 for 30 min and irradiated 24 h later, the timeframe when MnSOD activity levels were maximally elevated (Murley et al., 2007). Cells were exposed to 10 cGy of ionizing radiation using a Philips X-ray generator operating at 250 kVp and 15 mA at a dose rate of 0.6 cGy/sec. The frequency of induced instability is calculated as the number of GFP+/− colonies per total surviving colonies scored (Huang et al., 2004). Using this system, the inventor assessed whether RKO36 cells exhibit a thiol-induced adaptive response for the prevention of radiation-induced delayed genomic instability (delayed hyperrecombination). The results are shown in FIG. 2. A 10 cGy dose was not cytotoxic but it induced a significant elevation in the frequency of GFP+/− colonies over background, e.g., 2.7% vs 0.7%, P<0.001. The frequencies of GFP+/− colonies in 4 mM WR1065 treated cells or cells exposed to 10 cGy 24 h following treatment with 4 mM WR1065 were significantly lowered to 1.1% (P=0.02) and 1.6% (P=0.05) as compared to non-WR1065 exposed but irradiated cells, respectively.

Investigators have determined that with RKO36 cells, most GFP+/− mixed colonies are primarily composed of GFP− cells with varying numbers of GFP+ cells. The frequency of this induced genomic instability increases with dose, although typical of non-targeted effects, the dose response is not linear (Smith et al., 2003).

Figure 4A:
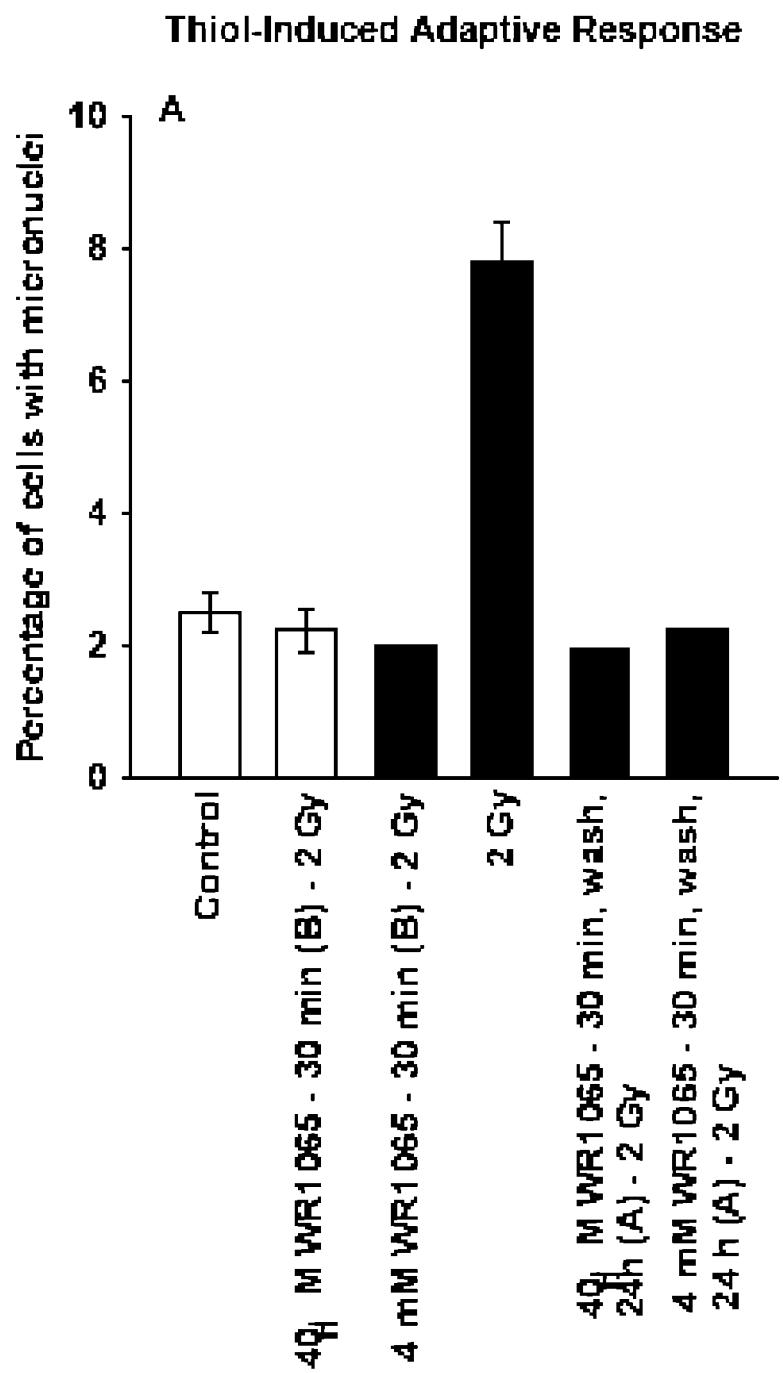
FIGS. 4A-B—Percentage of cells with micronuclei (A) treated with WR1065 and irradiated or irradiated 24 h after WR1065 exposure (B) treated with WR1065 at various times after irradiation.
Figure 4B:
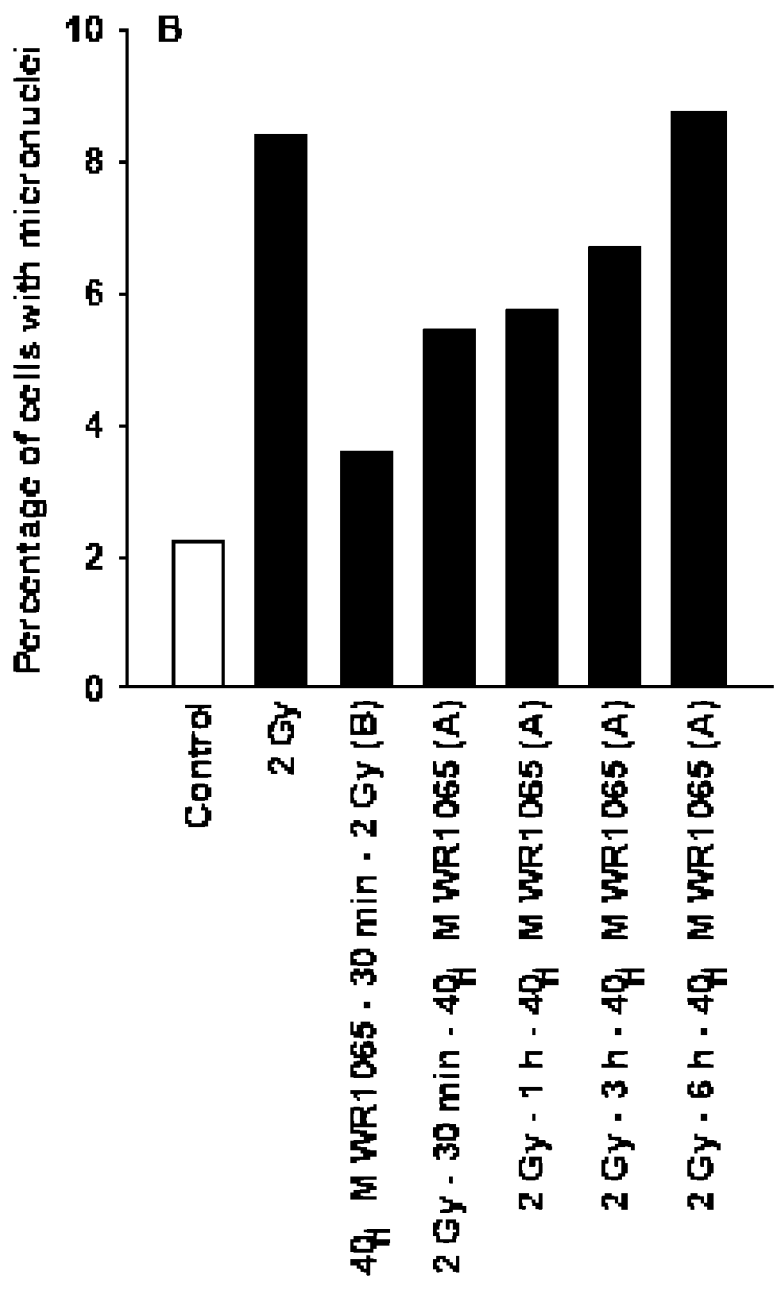
Figure 5:
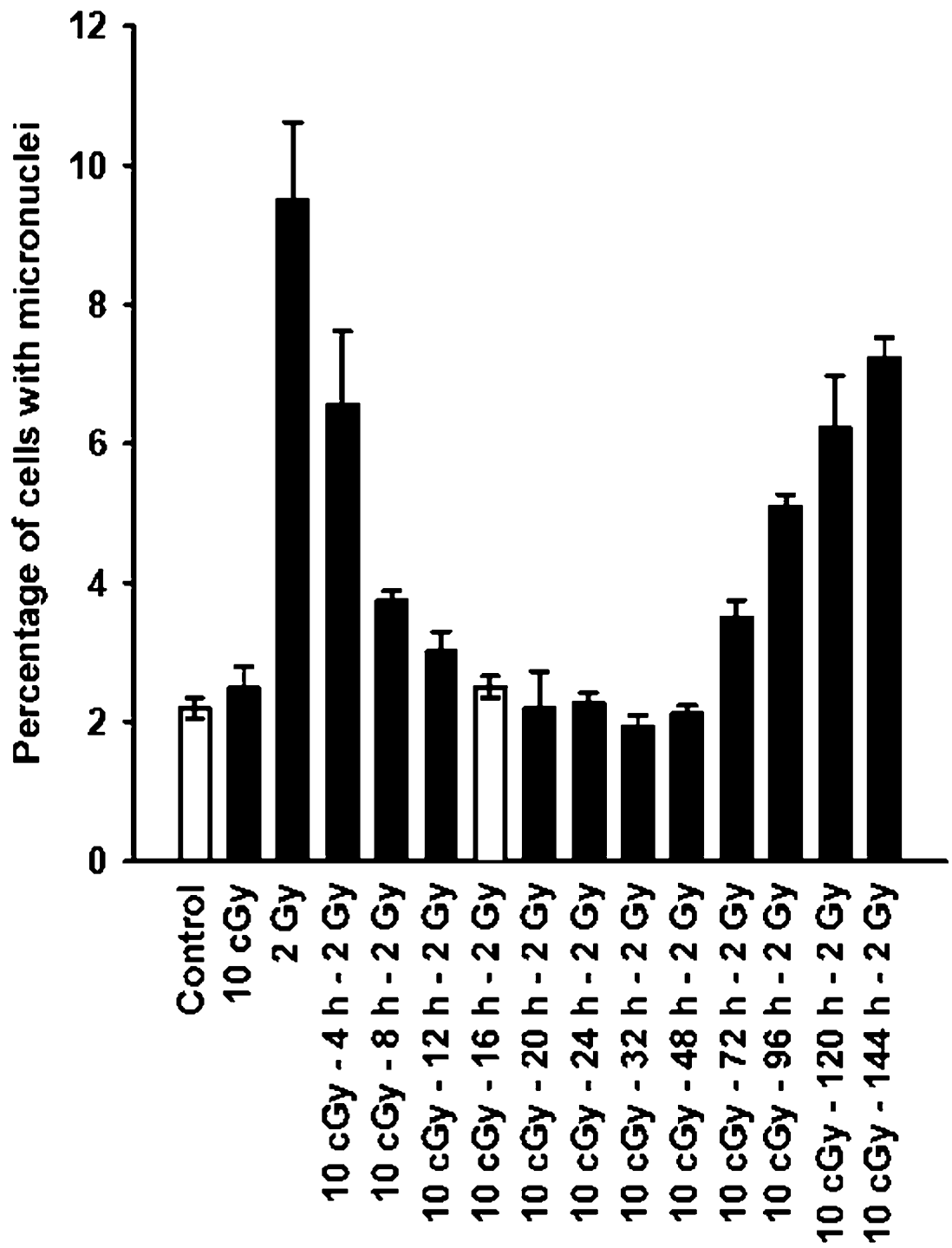
FIG. 5—Percentage of cells with micronuclei exposed to 10 cGy x-rays and challenged with 2 Gy various times later.

Example 2—Radiation-Induced Adaptive Responses on Micronuclei Formation in RKO36 Cells The frequency of micronuclei formation following a dose of 2 Gy was significantly reduced if cells were either exposed to WR1065 30 min or 24 h prior to irradiation (see FIG. 4A) or 30 min, 1, 2, or 3 h following irradiation (see FIG. 4B). Under the treatment conditions in which cells were exposed to WR1065 either 30 min before or 3 h following irradiation the protective effect is the result of a direct interaction between the thiol taken up by the cells and the damage induced by radiation. This direct protective effect disappeared when the drug was added 6 h following irradiation. However, when cells were exposed to the thiol 24 h prior to irradiation to allow for the induction of elevated MnSOD enzyme levels, a protective effect was again observed (see FIG. 5). In contrast to the data described in FIG. 4A, the protection described in FIG. 4B was mediated not directly by thiol action (Grdina et al., 1995) but as a result of a thiol-induced adaptive response mediated through the activation of NFκB resulting in the elevation of MnSOD activity (Murley et al., 2002; Murley et al., 2004; Murley et al., 2006; Murley et al., 2007; Murley et al., 2008). For comparison, a radiation-induced adaptive response was investigated by first exposing RKO36 cells to 10 cGy and then challenging with a 2 Gy dose 0, 4, 8, 12, 16, 20, and 24 h later (see FIG. 5). Both the thiol- and radiation-induced adaptive responses measured at 24 h following WR1065 or 10 cGy exposure, respectively, resulted in the reduction of micronuclei formation to unirradiated background levels.

Example 3—Thiol-Induced Elevated MnSOD Activity In Vivo

Figure 6:
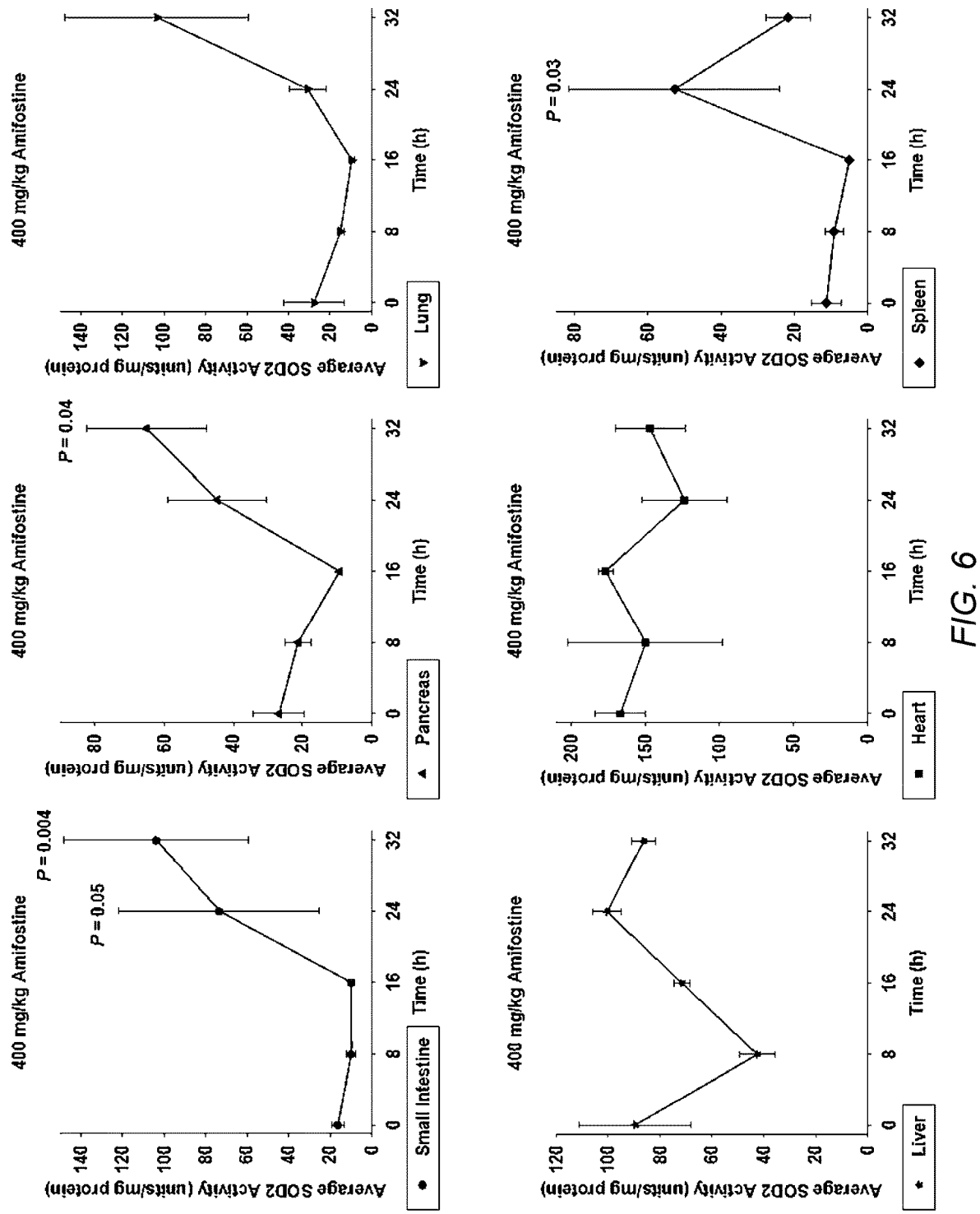
FIG. 6—Kinetics of effects of amifostine on MnSOD activity in normal mouse tissues.
Figure 7:
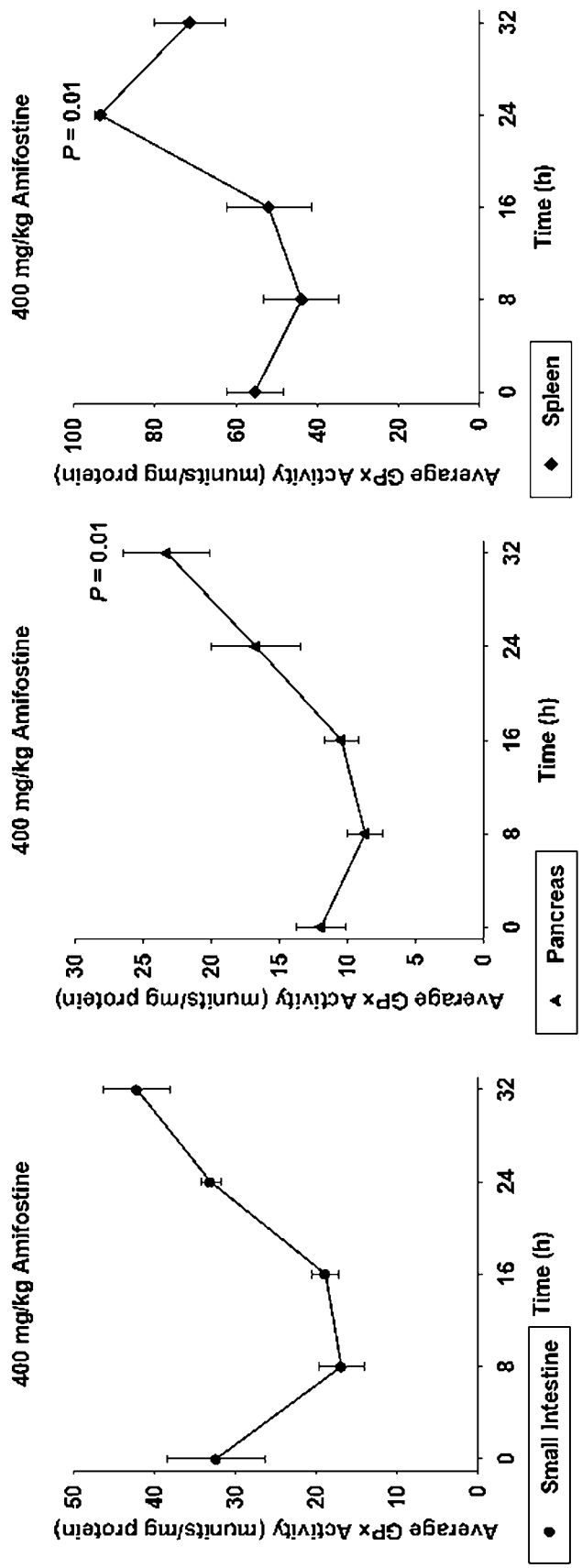
FIG. 7—Kinetics of effects of amifostine on GPx activity in normal mouse tissues.
Figure 8:
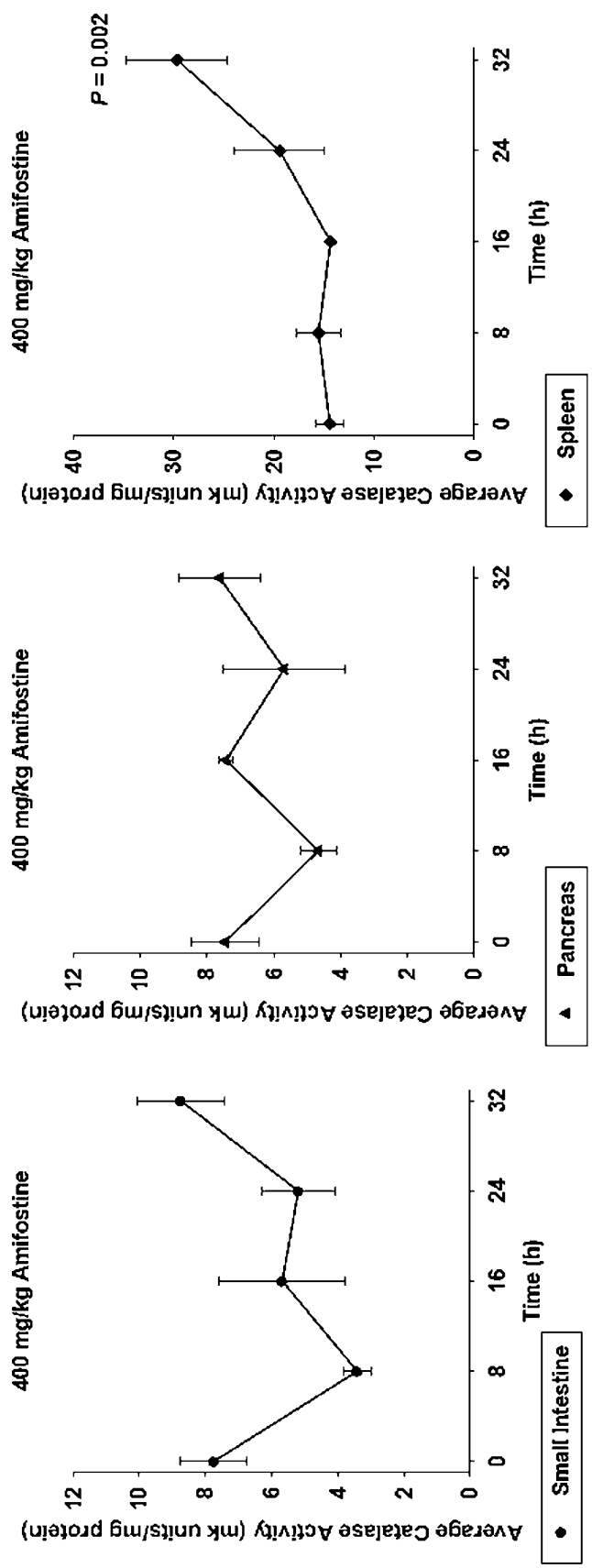
FIG. 8—Kinetics of effects of amifostine on catalase activity in normal mouse tissues.

In collaboration with the Free Radical Biology Core at The University of Iowa, the inventor characterized the activity of MnSOD in various normal tissues in C3H mice treated with amifostine, the prodrug form of WR1065. Animals at 60 days of age, three per experimental group, were injected i.p. with a single 400 mg/kg dose of amifostine (WR2721). Animals were sacrificed 8, 16, 24 and 32 h following amifostine administration and the small intestine, pancreas, lung, liver, heart and spleen of each animal was removed, flash frozen and coded. Coded samples were analyzed for MnSOD, catalase, and glutathione peroxidase (GPx) activity (Li et al., 1998; Oberley and Spitz, 1984). Presented in FIG. 6 are composite graphs demonstrating the effects of a single amifostine injection on the kinetics of change in MnSOD activity as a function of time. Pair-wise comparisons of the activities at the 0 h control and the time interval demonstrating the maximum enhancement or reduction in MnSOD activity were determined using a two-tailed Student's t test and are included. MnSOD activity was significantly elevated in small intestine, pancreas and spleen at either 24 h or 32 h. GPx activities were elevated in the spleen and pancreas at 24 h and 32 h, respectively (see FIG. 7), and catalase activity was elevated in the spleen at 32 h (see FIG. 8). These data demonstrate non-protein thiols can also affect MnSOD enzymatic activity in tissues in an animal model.

Example 4—In Vivo Inhibition of Micronuclei Formation

Figure 9:
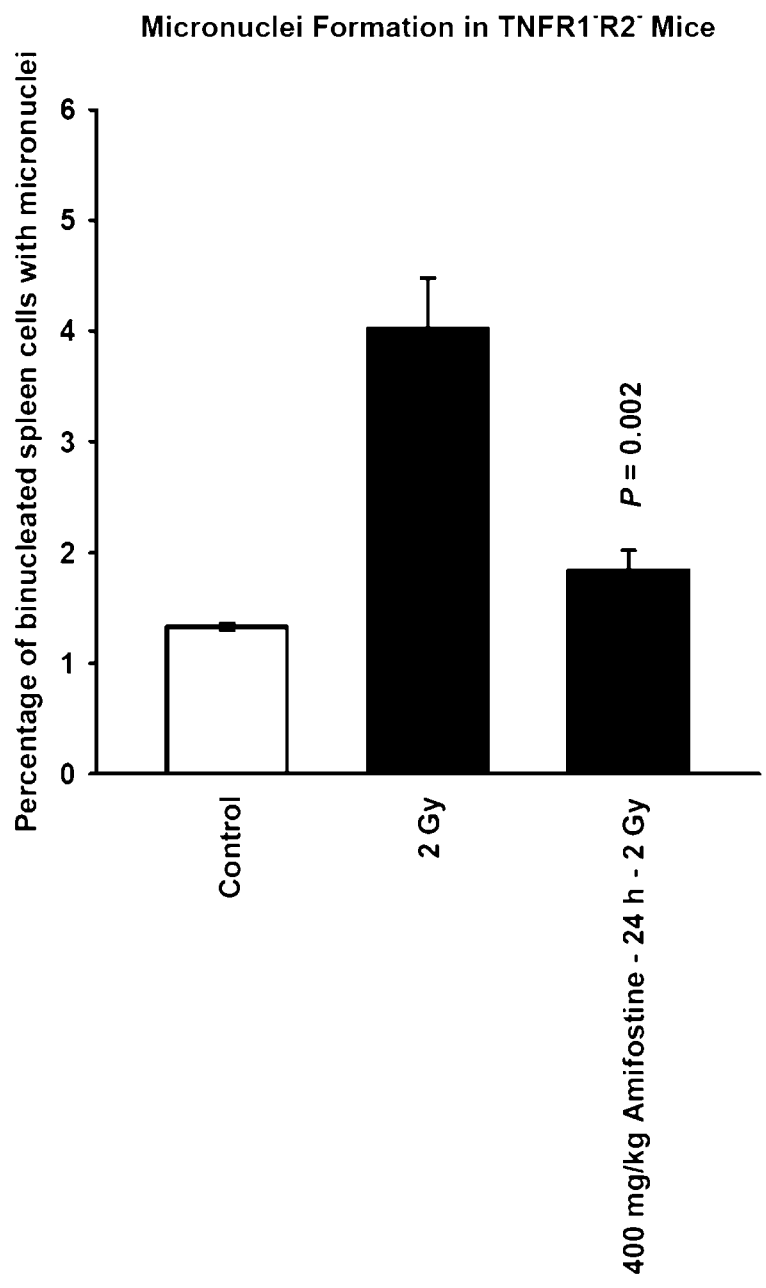
FIG. 9—Effects of amifostine on miocronuclei formation in normal mouse tissues.

C3H mice at 60 days of age, three per experimental group, were injected i.p. with a single 400 mg/kg dose of amifostine (WR2721). After 24 hours (when SOD2 activity was maximally elevated in the spleens of mice; see, Example 3), the mice were irradiated with 2 Gy of ionizing radiation, and spleen cells examined for micronuclei formation. FIG. 9 shows that miocronuclei formation was significantly inhibited in the amifostine treated animals as compared to non-amifostine treated control animals. It appears that amifostine can prevent genomic instability by directly stabilizing the genome, enhancing the fidelity of repair, slowing down cell cycle progression thereby facilitating repair before damage is fixed at cellular division, and by amifostine-induced SOD2 production in normal tissues. Increased intracellular SOD2 levels, through its endogenous anti-oxidant properties, can extend protection against genomic instability as evidenced by inhibition of micronuclei formation.

Figure 10A:
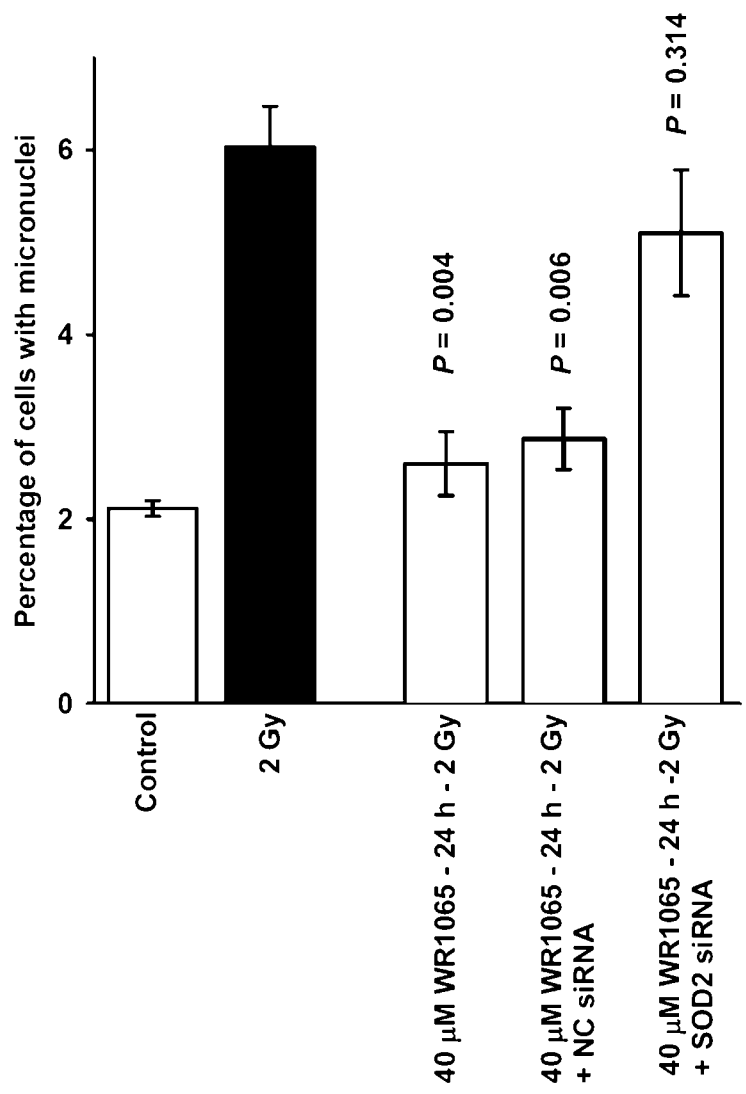
FIG. 10A-B—(A) Effects of SOD2-siRNA transfection on amifostine's ability to prevent radiation induced micronuclei formation; (B) Correspondence of SOD2-siRNA transfection with inhibition of elevated SOD2 activity.
Figure 10B:
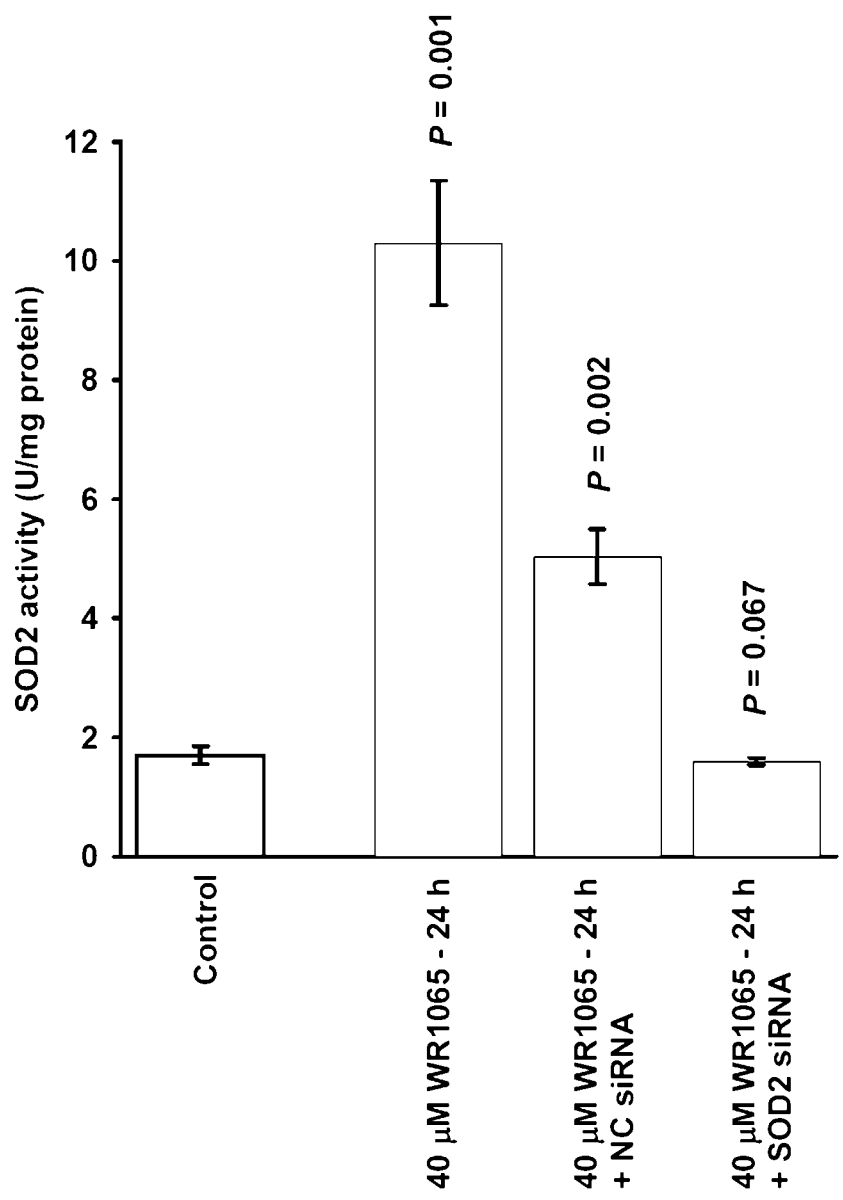

As further proof of the proposed mechanism of action, RKO human colon carcinoma cells (J. S. Murley et al. Radiat. Res. 175, 57-65, 2011; human microvascular endothelial cells (HMEC) and SA-NH mouse fibrosarcoma tumor cells (J. S. Murley et al. Radiat. Res. 169, 495-505, 2008) were transfected with SOD2-siRNA, (Ambion (Foster City, Calif.), the sequence of the SOD2-siRNA is 5' AAG GAA CAA CAG GCC TTA TTC 3')(SEQ ID NO:1) a specific inhibitor of SOD2 synthesis in cells. Control cells were transfected with siRNA that is not specific to SOD2 (nc-siRNA in FIGS. 10a and 10b). SOD2-siRNA transfection was found to inhibit amifostine's ability to prevent radiation induced micronuclei formation (see FIG. 10a). And, SOD2-siRNA transfection corresponded with inhibition of elevated SOD2 activity (see FIG. 10b). Thus, amifostine-induced SOD2 elevation can confer a protective property that adds to amifostine's usefulness as an antigenomic instability agent.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Morgan, *Radiat. Res.*, 159(5):581-596, 2003b.
Murley et al., *Radiat. Res.*, 158(1):101-109, 2002.
Murley et al., *Radiat. Res.*, 162:536-546, 2004.
Murley et al., *Free Radical. Biol. Med.*, 40:1004-1016, 2006.
Murley et al., *Radiat. Res.*, 167:465-474, 2007.
Murley et al., *Radiat. Res.*, 169:495-505, 2008.
Murley et al., *Radiat. Res.*, 175:57-65, 2011.
Nelson, In: *Thousands of New Cancers Predicted Due to Increased Use of CT*, Medscape, 2009.
Nickoloff, In: *Encyclopedia of Cancer*, Bertino (Ed.), Elsevier Science, $2^{nd}$ Ed., 4:49-59, 2002.
Oberley and Spitz, In: *Methods in Enzymology*, Packer (Ed.), Academic Press, 105:457-469, 1984.
Pamujula, S. et al., *J. Pharmacy Pharmacol.*, 56:1119-25, 2004.
Rothkamm et al., *Radiology*, 242:244-51, 2007.
Semelka et al., *J. Magn. Reson. Imaging*, 25(5):900-9, 2007.
Sigurdson et al., *Cancer Res.*, 68(21): 8825-8831, 2008.
Smith et al., *Health Phys.*, 85(1):23-29, 2003.
Srinivasan et al., *Int. J. Radiat. Biol.*, 78:535-543, 2002.
Sweeney, *Radiol. Technol.*, 51(3):321-7, 1979.
Tucker and Luckinbill, *Radiat Res.*, 175(5):631-7, 2011.

SEQUENCE LISTING

<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: Synthetic Primer

<400> SEQUENCE: 1
aaggaacaac aggccttatt c                                             21

V. REFERENCES

The following references, to the extent that they provide exemplary procedural or other details supplementary to those set forth herein, are specifically incorporated herein by reference.

U.S. Pat. No. 5,488,042
U.S. Pat. No. 5,567,686
U.S. Pat. No. 5,869,338
U.S. Pat. No. 5,891,856
U.S. Pat. No. 6,984,619
Bhatti et al., *Radiat. Environ. Biophys.*, 49(4):685-692, 2010.
Brenner et al., *Am. J. Roentgenol.*, 176(2):289-96, 2001.
Giambarresi and Jacobs, In: *Military Radiobiology*, Conklin and Walker (Eds.), Academic Press, 265-301, 1987.
Grdina et al., *Carcinogenesis*, 16(4):767-774, 1995.
Huang et al., *Molec. Cell. Biol.*, 24(11):5060-5068, 2004.
Jones et al., *Radiat. Res.*, 158(4):424-42, 2002.
Kataoka et al., *Radiat. Res.*, 168:106-11, 2007.
Khamsi, *New Scientist*, 11 May 2007.
Kim et al., *Cancer Res.*, 66:10377-10383, 2006.
Kumar et al., *Radiat. Res.*, 165(1): 43-50, 2006.
Lamperti et al., *Radiat. Res.*, 124:194-200, 1990.
Li et al., *Prostate*, 35:221-233, 1998.
Limoli et al., *Cancer Res.*, 57(18):4048-4056, 1997.
Marder and Morgan, *Mol. Cell. Biol.*, 13(11):6667-6677, 1993.
Morgan, *Radiat. Res.*, 159(5):567-580, 2003a.

What is claimed is:

1. A method of inhibiting genomic instability in a subject caused by computed tomography (CT) scan radiation comprising administering to the subject an effective dose of a phosphorothioate compound or derivative thereof prior to and/or following exposure to the CT scan radiation wherein the phosphorothioate compound or derivative thereof is selected from amifostine, WR-1065, WR-638, WR-3689, WR-2822, WR-2529, WR-77913, WR-255591, WR-2823, WR-33278, WR-255709, WR-151326, and WR-151327; wherein:
    the radiation dose is 1-25 cGy; and
    inhibiting genomic instability is selected from reducing micronuclei formation, reducing γ-H2AX formation, reducing chromosome translocation frequency, reducing HPRT mutant frequency, and reducing hyper-recombination.

2. The method of claim 1, wherein the phosphorothioate or derivative thereof is administered prior to exposure to the CT scan radiation.

3. The method of claim 1, wherein the phosphorothioate or derivative thereof is administered up to one hour following exposure to the CT scan radiation.

4. The method of claim 1, wherein the phosphorothioate or derivative thereof is administered prior and within 30 minutes after exposure to the CT scan radiation.

5. The method of claim 1, wherein the phosphorothioate or derivative thereof is amifostine or WR1065.

6. The method of claim 1, wherein the phosphorothioate or derivative thereof is administered subcutaneously, intravenously, topically, transdermally, orally, or using an auto-injector device.

7. The method of claim 1, wherein the subject has been diagnosed with cancer or is suspected of having cancer.

8. The method of claim 1, wherein the subject has had 1, 2 or 3 previous CT scans.

9. The method of claim 1, wherein the subject is a human or non-human animal.

10. The method of claim 1, wherein the antioxidant is selected from resveratrol, vitamin E, selenium, and catalase.

11. The method of claim 1, wherein the effective dose of a phosphorothioate compound or derivative thereof is administered prior to and/or up to 1, 2, or 3 hours following exposure to the CT scan radiation.

12. The method of claim 11, wherein further comprising diagnosing cancer in the subject using the computed tomography (CT) scan and/or treating the subject with cytoprotection.

13. A method of inhibiting genomic instability in a subject caused by diagnostic radiology procedures that involve exposure to ionizing radiation, comprising administering to the subject an effective dose of a phosphorothioate compound or derivative thereof prior to and/or following exposure to the diagnostic radiology procedure wherein the phosphorothioate compound or derivative thereof is selected from amifostine, WR-1065, WR-638, WR-3689, WR-2822, WR-2529, WR-77913, WR-255591, WR-2823, WR-33278, WR-255709, WR-151326, and WR-151327, wherein:
   the radiation dose is 1-25 cGy;
   inhibiting genomic instability is selected from reducing micronuclei formation, reducing γ-H2AX formation, reducing chromosome translocation frequency, reducing HPRT mutant frequency, and reducing hyper-recombination; and
   the diagnostic radiology procedure is selected from x-ray and computed tomography (CT).

14. The method of claim 2, wherein the phosphorothioate or derivative thereof is administered within 5 hours prior to exposure to the CT scan radiation.

15. The method of claim 1, wherein the genomic instability occurs within a 24-hour period after administration of the compound.

16. The method of claim 2, wherein the phosphorothioate or derivative thereof is administered at least 3 hours prior to exposure to the CT scan radiation.

17. The method of claim 1, wherein the CT scan radiation comprises ionizing radiation.

18. The method of claim 1, further comprising administering to the subject an antioxidant.

19. The method of claim 13, further comprising administering to the subject an antioxidant.

* * * * *